(12) United States Patent
Sun

(10) Patent No.: US 10,195,725 B2
(45) Date of Patent: Feb. 5, 2019

(54) ROTARY CLAMPING MECHANISM AND METHODS FOR USING THE SAME

(71) Applicant: SHANGHAI EASY-USE TOOLS ENTERPRISE CO., LTD, Shanghai (CN)

(72) Inventor: Shiyu Sun, Shanghai (CN)

(73) Assignee: SHANGHAI EASY-USE TOOLS ENTERPRISE CO., LTD, Shanghai (CN)

( * ) Notice: Subject to any disclaimer, the term of this patent is extended or adjusted under 35 U.S.C. 154(b) by 288 days.

(21) Appl. No.: 14/917,520

(22) PCT Filed: Nov. 6, 2013

(86) PCT No.: PCT/CN2013/086606
§ 371 (c)(1),
(2) Date: Mar. 8, 2016

(87) PCT Pub. No.: WO2015/058426
PCT Pub. Date: Apr. 30, 2015

(65) Prior Publication Data
US 2016/0214243 A1    Jul. 28, 2016

(30) Foreign Application Priority Data

Oct. 21, 2013   (CN) .......................... 2013 1 0496629

(51) Int. Cl.
*B25B 27/02*    (2006.01)
*B25B 27/04*    (2006.01)
*B25B 13/56*    (2006.01)
*A61B 17/3217*  (2006.01)
*B23D 51/10*    (2006.01)
*B26B 5/00*     (2006.01)
(Continued)

(52) U.S. Cl.
CPC .............. *B25B 27/02* (2013.01); *B25B 13/56* (2013.01); *B25B 27/04* (2013.01);
(Continued)

(58) Field of Classification Search
CPC ....... B44B 11/00; B44B 2700/12; B25B 3/00; B25B 9/00–9/04; B25B 27/00;
(Continued)

(56) References Cited

U.S. PATENT DOCUMENTS 3,373,491 A * 3/1968 Montelius .......... A61B 17/3213
                                                   30/339
4,121,329 A * 10/1978 Sugiyama .......... A61B 17/3215
                                                   29/270
(Continued)

FOREIGN PATENT DOCUMENTS

CN    202318079 U     7/2012
CN    102729184 A    10/2012
(Continued)

OTHER PUBLICATIONS

Translation of CN103342076, generated Jun. 21, 2018.*
International Search Report in corresponding PCT Application No. PCT/CN2013/086606, dated Jul. 25, 2014.

*Primary Examiner* — Matthew P Travers
(74) *Attorney, Agent, or Firm* — Leason Ellis LLP

(57) ABSTRACT

This invention discloses a rotary clamping mechanism comprising a cylinder, a rotary member, and a clamping member, wherein the rotary member and the clamping member have shapes that gradually change; the rotary member comprises a first board, a second board, a first connection member, and a second connection member; a wall groove is arranged at the lower side of the inner wall of the cylinder; the rotary member and the clamping member can rotate in the cylinder to contract and compress.

1 Claim, 22 Drawing Sheets

(52) U.S. Cl.
CPC .......... *A61B 17/3217* (2013.01); *B23D 51/10* (2013.01); *B26B 5/00* (2013.01)

(58) Field of Classification Search
CPC ......... B25B 27/02; B25B 27/04; B25B 33/00; A61B 17/3217; B26B 5/00; B23B 31/18; B23D 51/08–51/10
USPC .......................................................... 30/541
See application file for complete search history.

(56) References Cited

U.S. PATENT DOCUMENTS

| | | | | |
|---|---|---|---|---|
| 4,127,224 A | * | 11/1978 | Newman, Sr. .......... | B23B 31/18 226/196.1 |
| 4,244,094 A | * | 1/1981 | Rucinski ............ | A61B 17/3217 29/270 |
| 5,255,422 A | * | 10/1993 | Russo ................. | A61B 17/3217 269/6 |
| 5,454,534 A | * | 10/1995 | Baskas ............... | A61B 17/3215 211/70.7 |
| 7,251,897 B2 | * | 8/2007 | Shuhua .................. | B23D 51/10 279/71 |
| 7,871,080 B2 | * | 1/2011 | Marini .................. | B23D 51/10 279/140 |
| 8,181,973 B2 | * | 5/2012 | Dezheng ................ | B23D 51/10 279/71 |
| 9,744,605 B2 | * | 8/2017 | Wang ..................... | B23D 51/10 |
| 2011/0314664 A1 | | 2/2011 | Matsumoto et al. | |
| 2011/0226645 A1 | * | 9/2011 | Kierce ............... | A61B 17/3215 206/349 |

FOREIGN PATENT DOCUMENTS

| | | |
|---|---|---|
| CN | 103342076 A | 10/2013 |
| JP | 2009-262256 A | 12/2009 |

\* cited by examiner

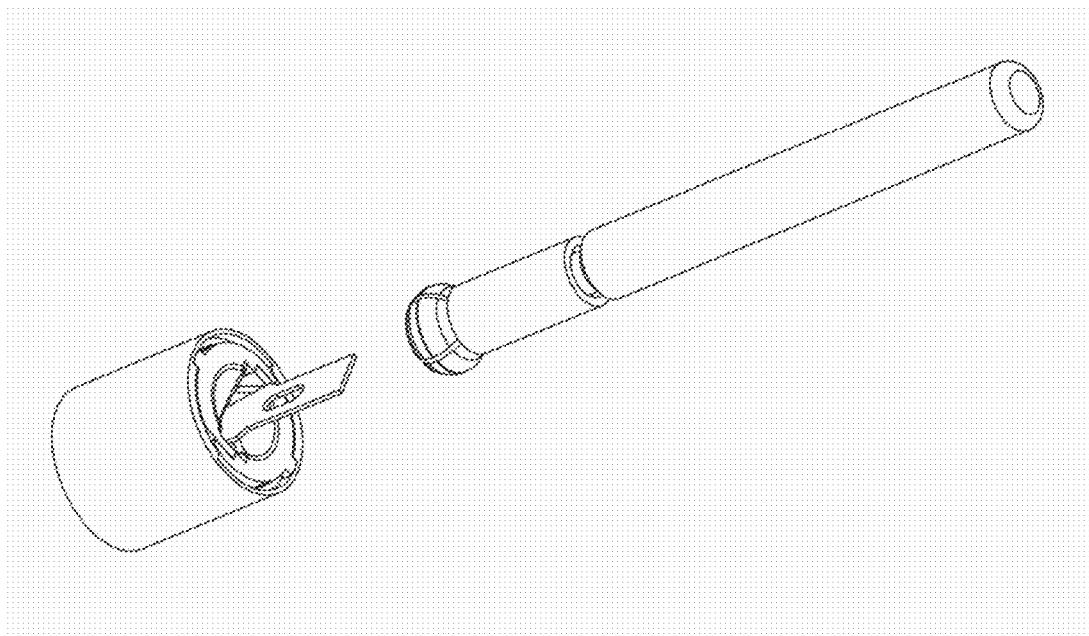

Figure 4C

| step 1, inserting a blade into a small seam between the first board and the second board; |
|---|

↓

| step 2, rotating the first connection member and the second connection member, and clamping the blade by the clinging of the first connection member and the second connection member; |
|---|

↓

| step 3, pulling out the blade from a cutter arbor, and putting the rotary clamping mechanism clamping the blade into a tool kit. |
|---|

Figure 5 step 1, inserting a bit into the clamping member ;

step 2, rotating the clamping member, and clamping the bit tightly by a convergent force between the lower sliding blocks of the clamping member;

step 3, pulling out the bit from the cutter arbor, and putting the rotary clamping mechanism clamping the blade into a tool kit.

Figure 18

ROTARY CLAMPING MECHANISM AND METHODS FOR USING THE SAME

CROSS-REFERENCE TO RELATED PATENT APPLICATIONS

This application is a U.S. National Phase Application under 35 U.S.C. § 371 of International Patent Application No. PCT/CN2013/086606, filed Nov. 6, 2013, and claims the priority of the Chinese Application No. 201310496629.5, filed Oct. 21, 2013, all of which are incorporated by reference in their entireties. The International Application was published on Apr. 30, 2015 as International Publication No. WO 2015/058426 A1.

BACKGROUND OF THE INVENTION

1. Field of the Invention

The invention relates to cutter clamping devices, more specifically, to a rotary clamping mechanism and methods for using the same.

2. Description of the Related Art

It is well-known that blades of sculpture blades are inserted in the cutter arbors; when blades are not in use, it needs to be taken down and stored for protecting blades. However, to take blades down, it is common that people touch the blades by their hands directly, which easily makes blades rust caused by sweat in hand. Meanwhile, the action of taking blades down may have the risk of scratching users' hands; if a glove is worn, taking blades down may also ruin the glove; and more importantly, not everyone has the force to pull out the blades from the cutter arbors. The aforementioned reasons make the action of taking blades down from sculpture blades encountered a few difficulties. Besides, in the process of positioning blades, it usually needs two hands to complete the process, which seems very inconvenient from time to time.

SUMMARY OF THE INVENTION

This invention discloses a rotary clamping mechanism and methods for using the same, which is used to solve the problems of taking a blade from sculpture blade and storing blade after being taken from the sculpture blade in prior art.

To achieve the above purposes, the technical scheme used by the invention is:

a rotary clamping mechanism comprising a cylinder and a rotary member, wherein the rotary member has a shape of gradual change; a wall groove is arranged at the lower side of the inner wall of the cylinder; a lower side of the rotary member touches against the inside of the wall groove and rotates to contract and compress.

In the aforementioned rotary clamping mechanism, wherein, the rotary member comprises a first board, a second board, a first connection member, and a second connection member; the first connection member is configured at one end of the first board; the second connection member is configured at one end of the second board; and the first connection member is connected with the second connection member; the first board is reversed bending with respect to the second board and presents a shape of arc; an extruded body is configured by outwardly extruding one end of the first board which is far from the first connection member along a bending surface of the first board; a bump is configured at middle of an end of the extruded body; the first connection member presents a shape of half circular disc; outer surfaces of arc-shaped surfaces of the first connection member is configured respectively with an inserting hole and an insert; a shape of the first connection member is as same as a shape of the second connection member; the shape of the first board matches with the shape of the second board; the insert of the first connection member is configured inside the inserting hole of the second connection member; the insert of the second connection member is configured inside the inserting hole of the first connection member; the upper edge of an inner wall of the cylinder is configured with a wall groove; the lower edge of the inner wall of the cylinder is configured with two arc-shaped blocks; two corresponding sides of the upper edge of the wall groove both are configured with arc-shaped grooves, and the arc-shaped grooves are configured in a stagger way with the arc-shaped blocks.

In the aforementioned rotary clamping mechanism, wherein, two strip grooves are configured at a lower part of the inner wall of the cylinder, and the two strip grooves extend from a middle part of the inner wall of the cylinder to the lower edge of the cylinder.

In the aforementioned rotary clamping mechanism, wherein, an outer side of the arc-shaped surface of the first connection member is configured with a sliding block, configured at a middle part of the arc-shaped surface.

In the aforementioned rotary clamping mechanism, wherein, the rotary piece is an integral clamping member; an upper part of the clamping member is provided with two upper sliding blocks and a lower part of the clamping member is provided with two lower sliding blocks.

A method for using the rotary clamping mechanism comprises connecting the first connection member and the second member, and placing the first connection member and the second connection member into the cylinder, and the method further comprises:

step 1, inserting a blade into a small seam between the first board and the second board;

step 2, rotating the first connection member and the second connection member, and clamping the blade by the clinging of the first connection member and the second connection member;

step 3, pulling out the blade from a cutter arbor, and putting the rotary clamping mechanism clamping the blade into a tool kit.

A method for using the rotary clamping mechanism, wherein, comprises placing the clamping member into the cylinder, and the method further comprises:

step 1, inserting the a bit into the clamping member; step 2, rotating the clamping member, and clamping the bit tightly by a convergent force between the lower sliding blocks of the clamping member;

step 3, pulling out the bit from the cutter arbor, and putting the rotary clamping mechanism clamping the blade into a tool kit.

By using the methods for using the rotary clamping mechanism of the invention, it has the beneficial effect as follows: blades can be pulled out of cutter arbors easily, and be prevented from rusting caused by touching of hand sweating and blades when depositing blades; meanwhile, it prevents fingers from being scratched; it is easy in operation, and simple in structure which makes the mechanism convenient to manufacture.

BRIEF DESCRIPTIONS OF THE DRAWINGS

Referring to the following drawings and the description of the non-restrictive embodiments, the additional features, purposes and advantages of the invention can be more obvious:

FIGS. 4A to 4C are using state diagrams of a rotary clamping mechanism of the invention;

FIG. 5 is a flow chart of a method for using a rotary clamping mechanism of the invention;

FIG. 18 is a flow chart of using another rotary clamping mechanism of the invention.

Figure 1:
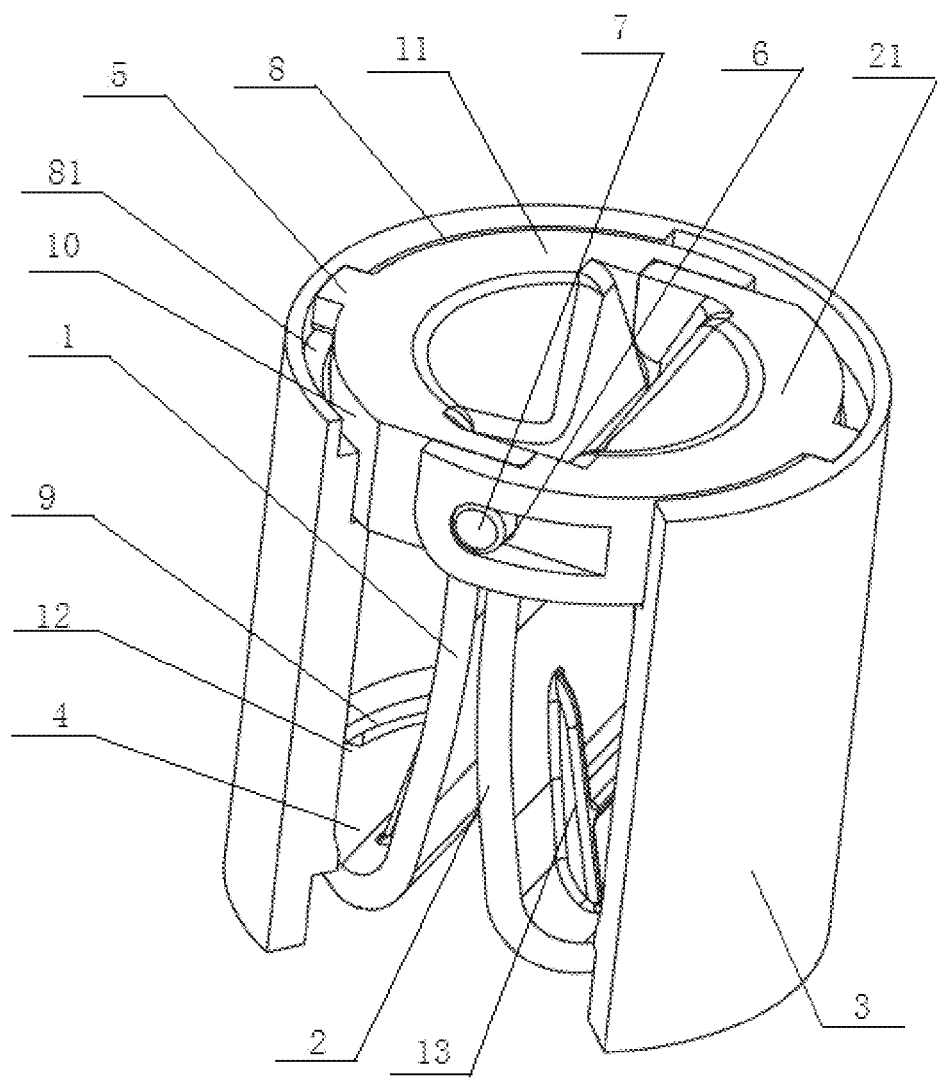
FIG. 1 is a space cutaway schematic diagram of a rotary clamping mechanism of the invention.

Reference in the drawings: First board 1, first connection member 11, second board 2, second connection member 21, cylinder 3, extruded body 4, sliding block 5, inserting hole 6, insert 7, wall groove 8, arc-shaped groove 81, two arc-shaped block 9, arc-shaped surface 10, bump 12, stiffener 13, strip groove 14, clamping member 15, upper sliding block 16, lower sliding blocks 17, bit 21.

DETAILED DESCRIPTION

Hereinafter, certain exemplary embodiments according to the present invention will be described with reference to the accompanying drawings, so as to make the technical means, inventive features, purpose and effect of the invention easier to understand.

Figure 2:
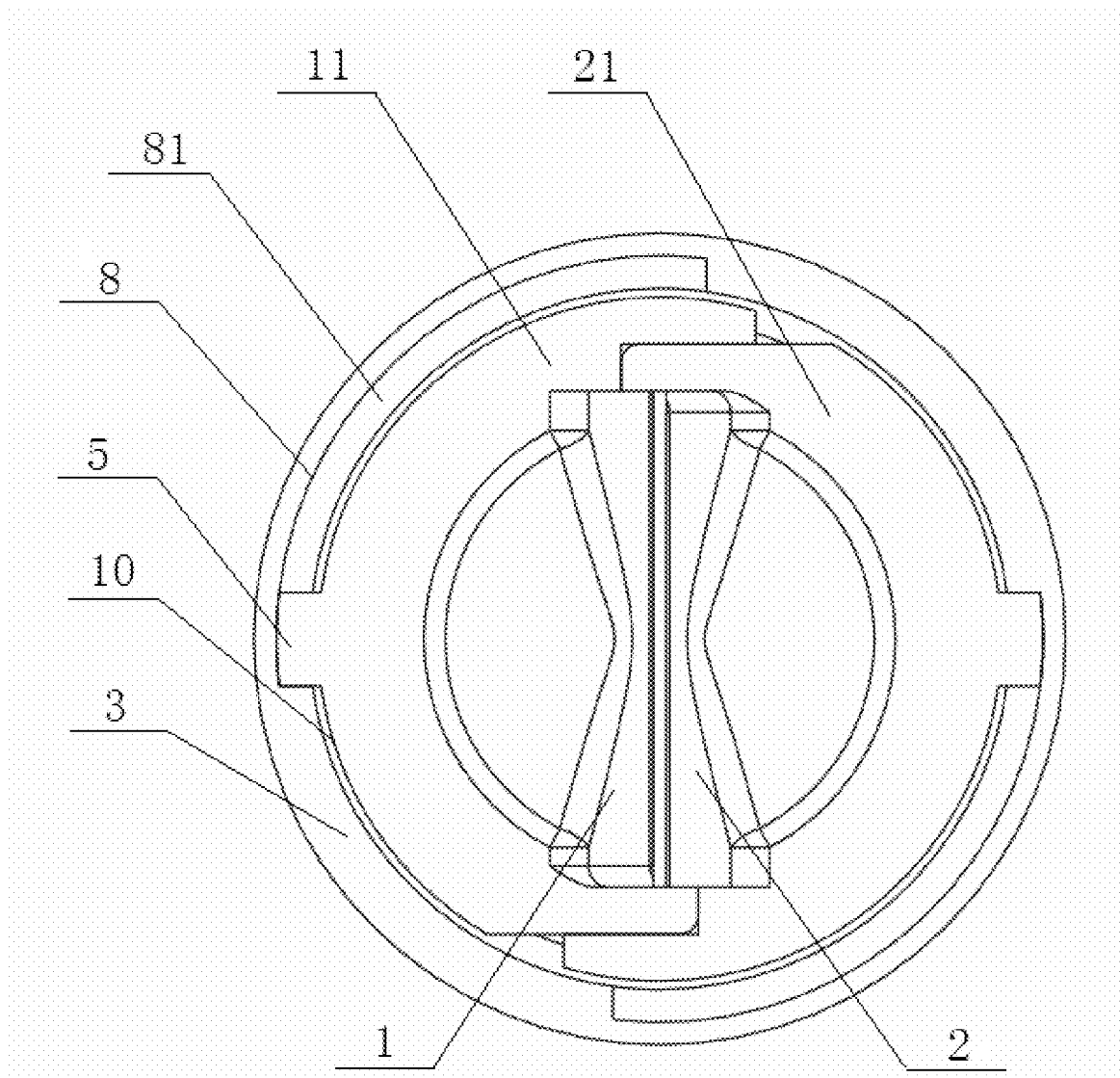
FIG. 2 is a top view of a rotary clamping mechanism of the invention.
Figure 3:
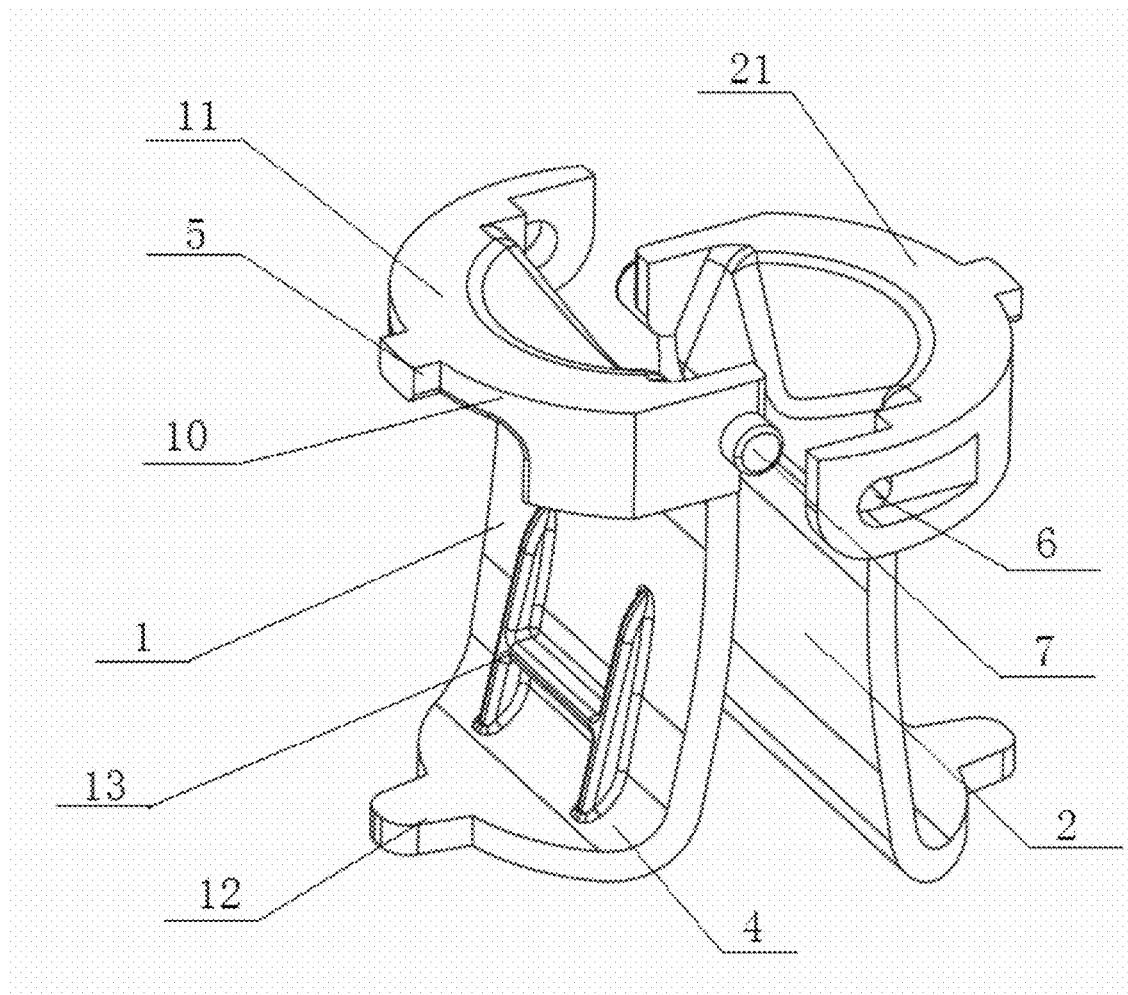
FIG. 3 is a schematic diagram of a first connection member and a second connection member of a rotary clamping mechanism of the invention.
Figure 4A:
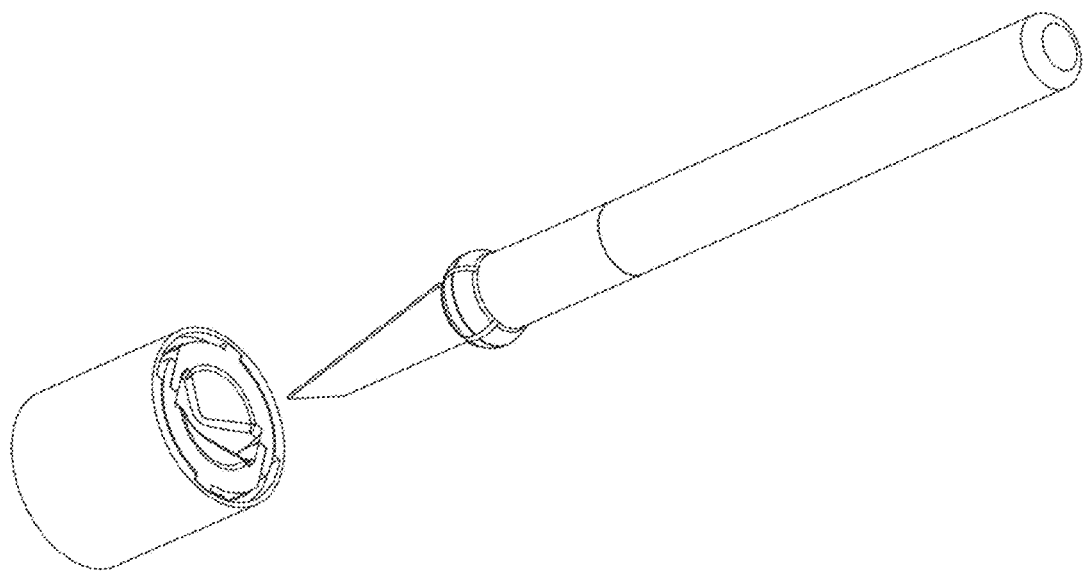
Figure 4B:
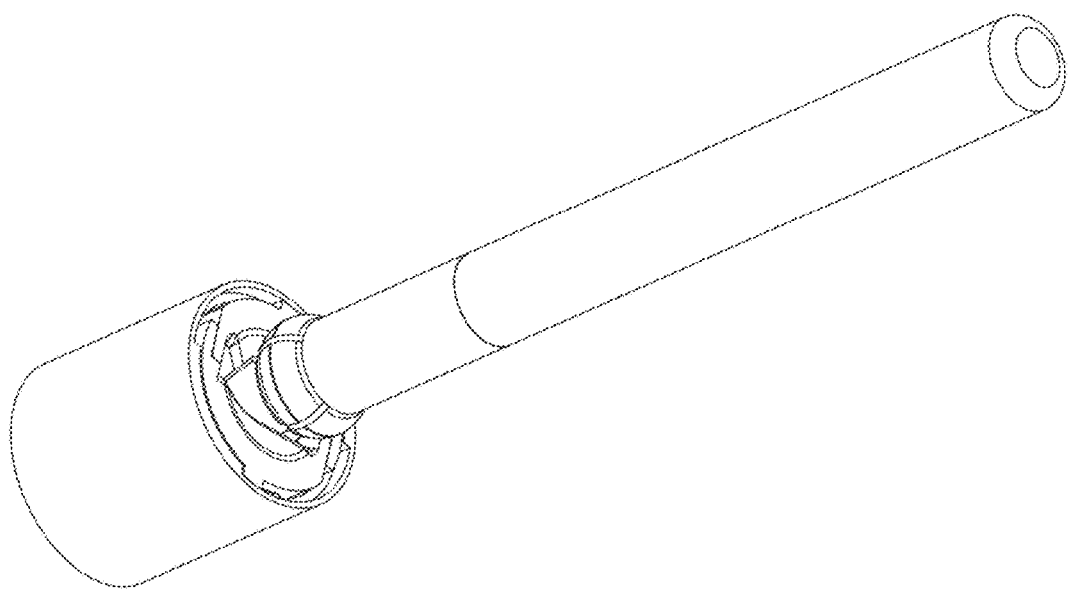

FIGS. 1 to 3 show a rotary clamping mechanism comprising a cylinder 3 and a rotary member, wherein the rotary member has a shape of gradual change; a wall groove 8 is arranged at the lower side of the inner wall of the cylinder 3; a lower side of the rotary member touches against the inside of the wall groove 8 and rotates to contract and compress.

In an embodiment of the invention, for a rotary clamping mechanism, wherein, the rotary member comprises a first board 1, a second board 2, a first connection member 11, and a second connection member 21; the first connection member 11 is configured at one end of the first board 1; the second connection 2 member is configured at one end of the second board 21; and the first connection 11 is connected with the second connection member 21; the first board 1, the second board 2, the first connection member 11 and the second connection member 21 are all configured inside the cylinder 3. The first board 1 is reversed bending with respect to the second board 2 and presents a shape of arc; further, after the first connection member 11 is connected to the second connection member 21, the first board 1 and the second board 2 are out of touch mutually.

An extruded body 4 is configured by outwardly extruding one end of the first board 1 which is far from the first connection member 11 along a bending surface of the first board 1; the first connection member 11 presents a shape of half circular disc; outer surfaces of arc-shaped surfaces 10 of the first connection member 11 is configured respectively with an inserting hole 6 and an insert 7; a shape of the first connection member 11 is as same as a shape of the second connection member 21; the shape of the first board 1 matches with the shape of the second board 2; the insert 7 of the first connection member 11 is configured inside the inserting hole 6 of the second connection member 21; the insert 7 of the second connection 21 member is configured inside the inserting hole 6 of the first connection member 11; The upper edge of the inner wall of the cylinder 3 is configured with a wall groove 8; further, the wall groove 8 makes lower sides of the connected first connection member 11 and the connected second connection member 21 touch against the inside of the wall groove 8; the lower edge of the inner wall of the cylinder 3 is configured with two arc-shaped blocks 9.

In an embodiment of the invention, two corresponding sides of the upper edge of the wall groove 8 both are configured with arc-shaped grooves 81, of which the length is one fourth of the perimeter of the upper edge of the cylinder 3, and the arc-shaped grooves are configured in a stagger way with the arc-shaped blocks.

In an embodiment of the invention, an outside of the arc-shaped surface 10 of the first connection member 11 is configured with a sliding block 5, which is configured in the middle of the arc-shaped surface. Further, the sliding block 5 is slidingly embedded in the arc-shaped groove 81, which limits the sliding range of the sliding block 5.

In an embodiment of the invention, a bump 12 is configured at middle of an end of the extruded body 4; further, it slides between the lower edge of the cylinder 3 and the inner wall of the arc-shaped block 9 through the bump 12.

In an embodiment of the invention, a stiffener 13 is configured between the middle of the first board 1 and the connection of the extruded body 4, and the stiffener 13 presents a shape of "I".

In an embodiment of the invention, the length of connected the first connection member 11 and the first board 1 is the same as the height of cylinder 3, and the outside of the end face of the extruded body 4 is flush with the inner wall of the arc-faced piece 9. Further, as the first connection member 11 and the second connection member 21 are screwed into the cylinder 3, they match with the cylinder 3.

As shown in FIG. 5, a rotary clamping mechanism and methods for using the same comprise placing the connected first connection member 11 and the connected second connection member 21 into the cylinder 3, and the method has the following specific step 1, inserting a blade into a small seam between the first board 1 and the second board 2;

step 2, rotating the first connection member and the second connection member, and clamping the blade by the clinging of the first connection member and the second connection member;

step 3, pulling out the blade from a cutter arbor, and putting the rotary clamping mechanism clamping the blade into a tool kit.

As shown in FIGS. 4A to 4C and 5, in the embodiment of this invention, insert a blade into the first board 1 and the second board 2 of the cylinder 3; rotate the first connection member 11, the second connection member 21 or the handle of the blade to make the extruded body 4 move towards the arc-shaped block 9; with the pressure of the arc-shaped block 9, the blade is clamped by the clinging of the first connection member 1 and the second connection member 2; pull the blade out of the handle of the blade by using the clamp force of the first board 1 and the second board 2.

Figure 6:
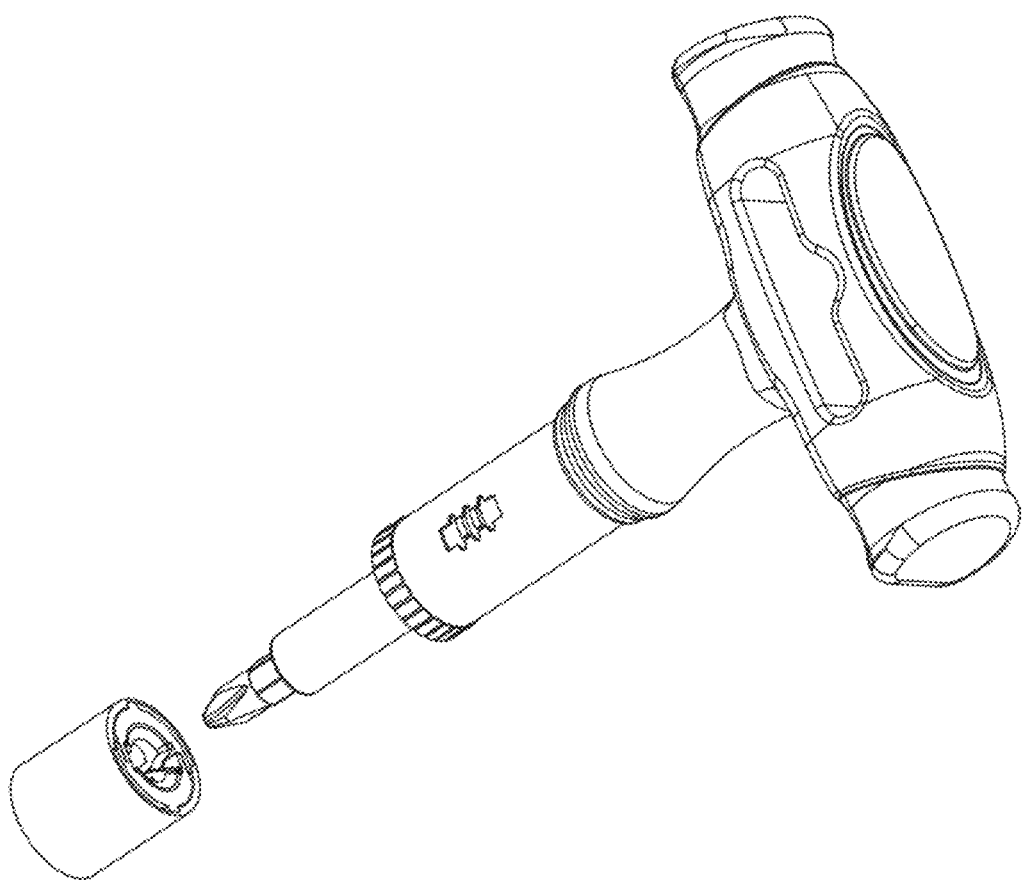
FIG. 6 is a schematic diagram of dismounting a bit from a rotary clamping mechanism of the invention.

As shown in FIG. 6, in another embodiment of the invention, both the joint of the first board 1 and the first connection member 11 and the joint of the second board 2 and the second connection member 21 present a shape of "T", and when the first board 1 is combined with the second board 2, the joint thereof presents a shape of a cross. Rotate the first connection member 11 and the second connection member 21 to make the first board 1 and the second board 2 mutually clamps a cross thread bit, and dismount the cross thread bit from the handle.

Figure 7:
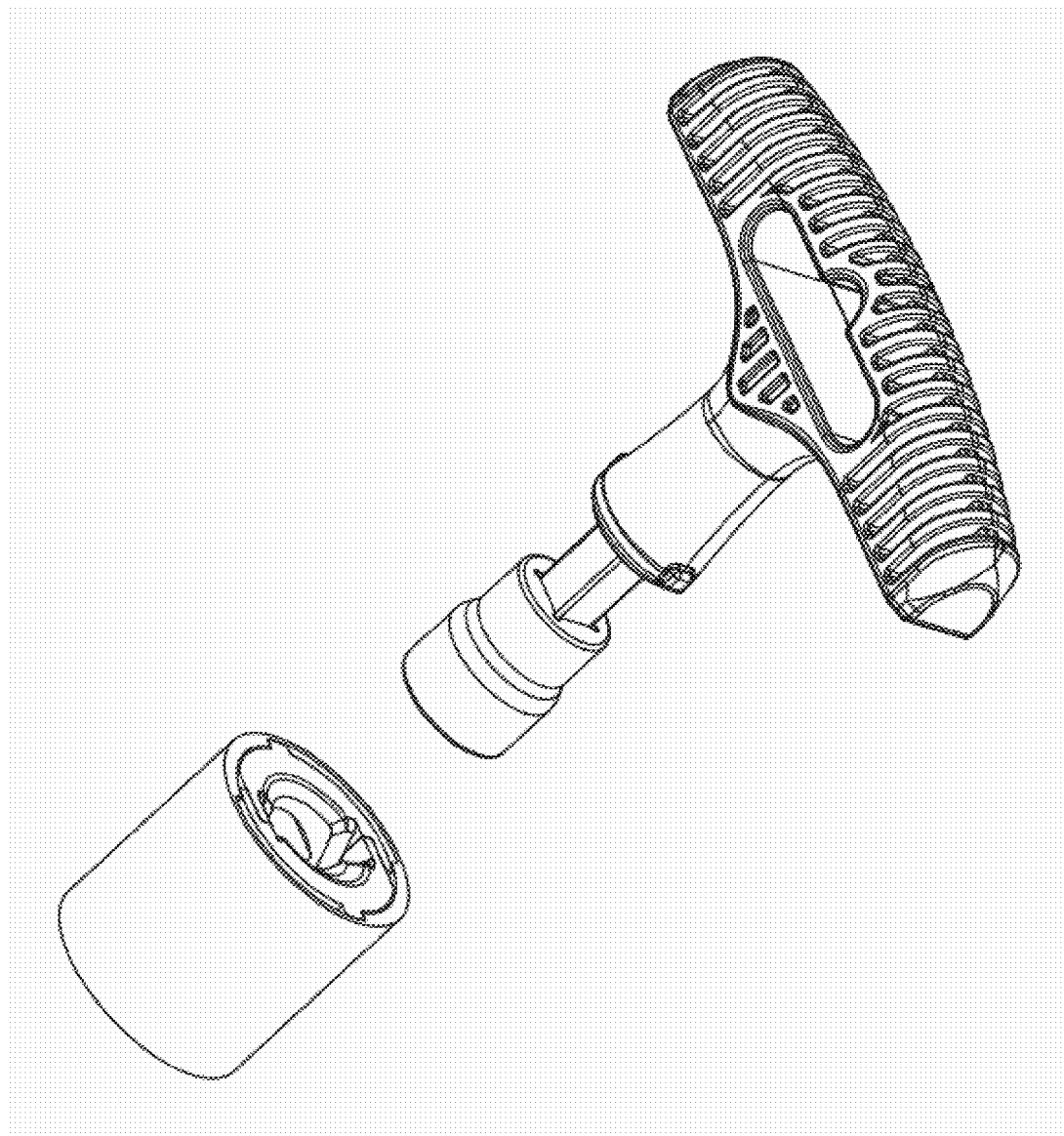
FIG. 7 is a schematic diagram of dismounting a cylinder from a rotary clamping mechanism of the invention.
Figure 8A:
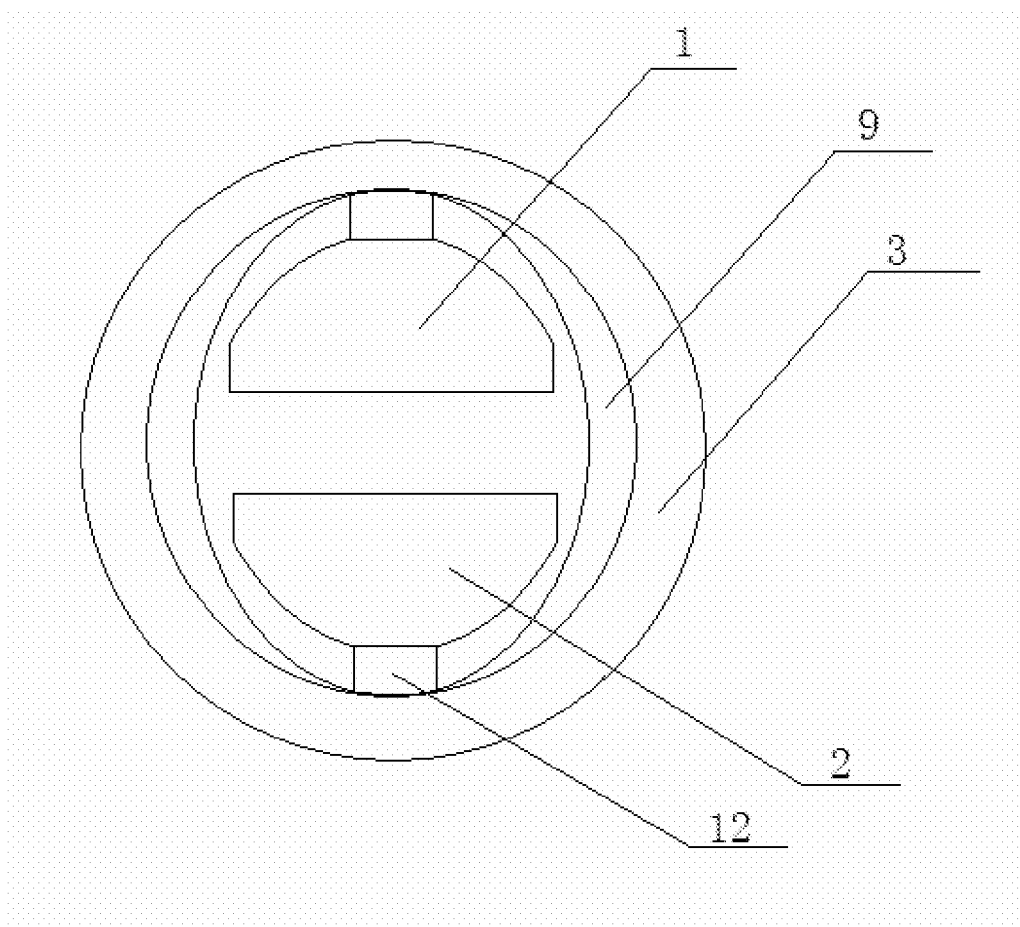
FIGS. 8A to 8B are schematic bottom views of a dismounting cylinder with a structure of arc-shaped block of a rotary clamping mechanism of the invention.
Figure 8B:
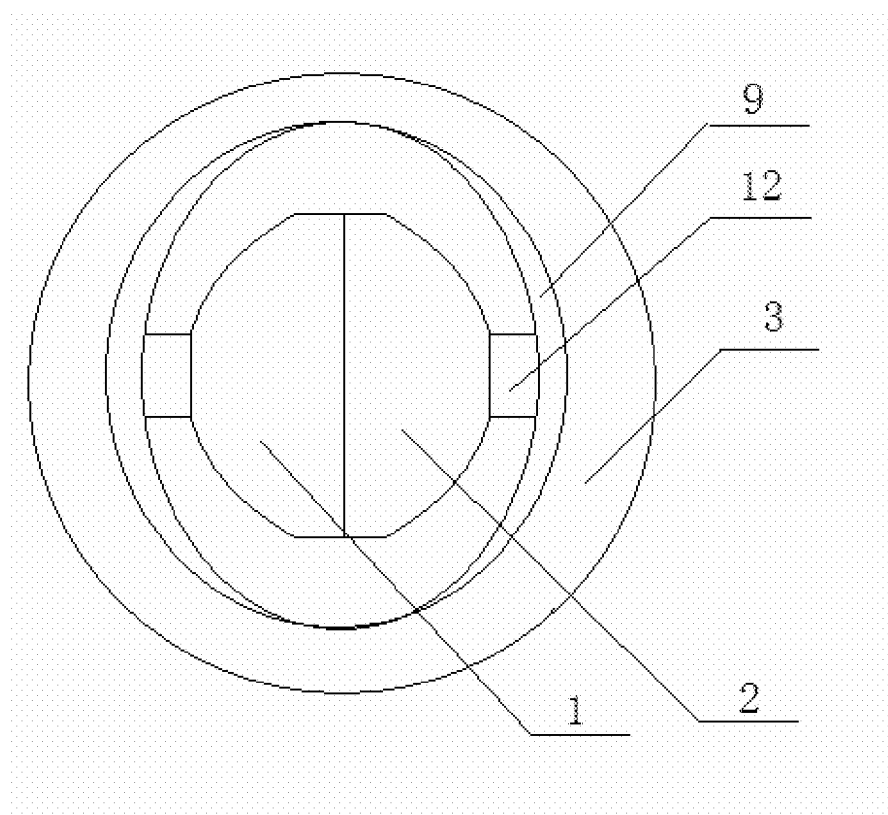
Figure 9A:
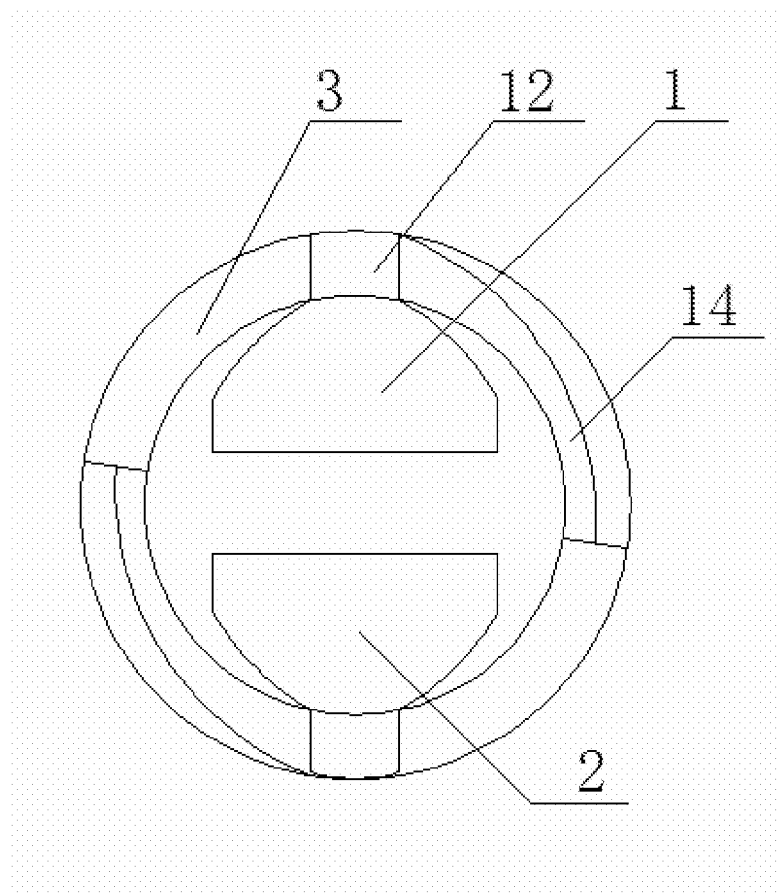
FIGS. 9A to 9D are structure diagram of a dismounting cylinder with a structure of strip groove of a rotary clamping mechanism of the invention.
Figure 9B:
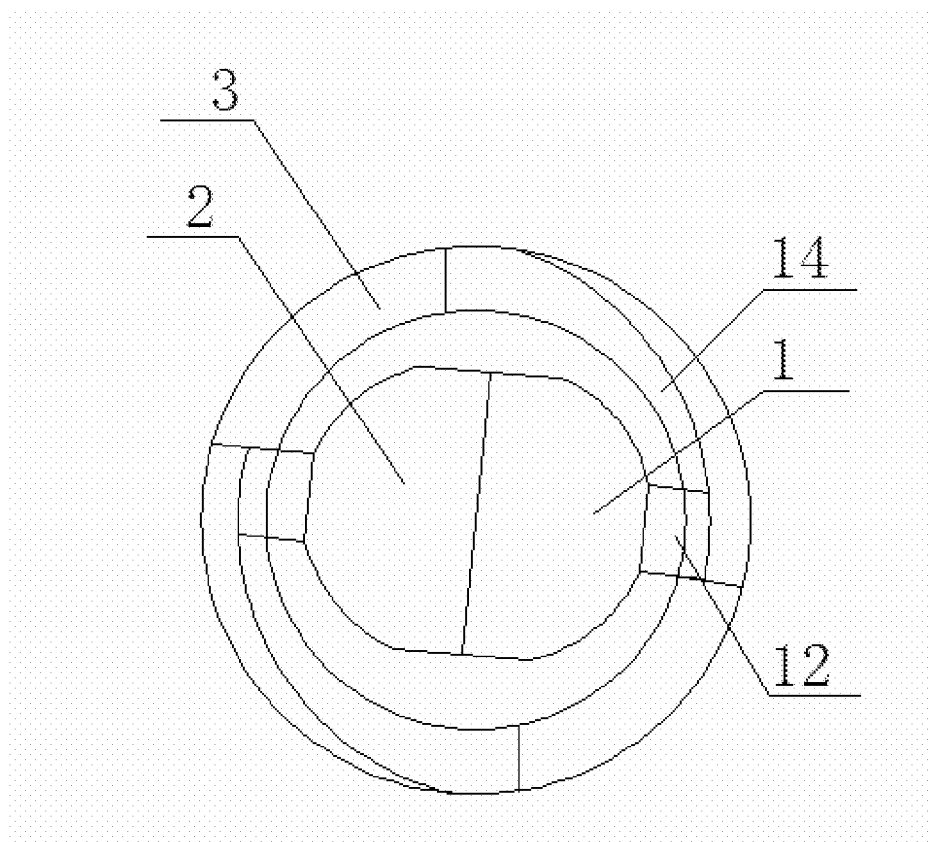
Figure 9C:
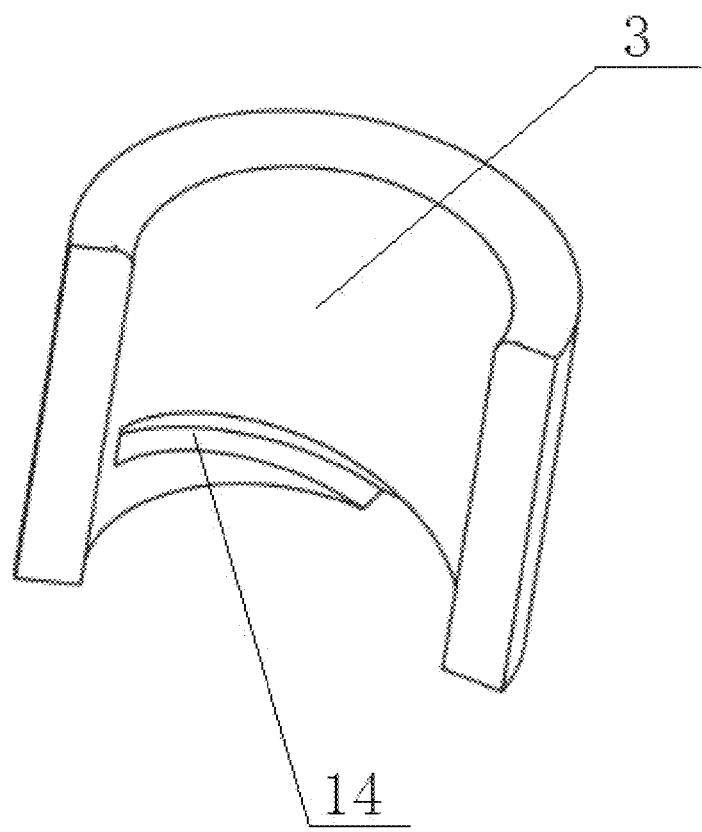
Figure 9D:
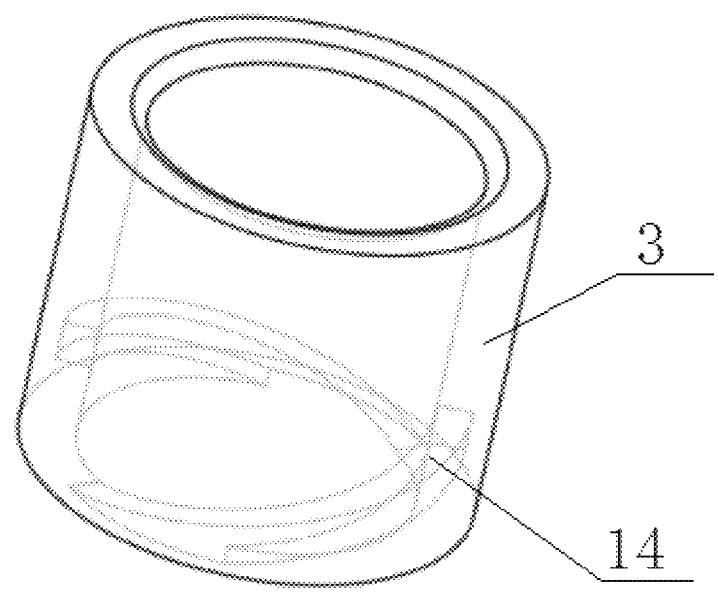

As shown in FIG. 7, in another embodiment of the invention, both the joint of the first board 1 and the first connection member 11 and the joint of the second board 2 and the second connection member 2 present semicircular in shape, and when the first board 1 is combined with the second board 2, the joint thereof presents a shape of circular. Rotate the first connection member 11 and the second connection member 21 to make the first connection member 11 and the second connection member 21 mutually clamp the cylinder, and dismount the cylinder from the handle.

In an embodiment of the invention, with changes of the shape of the joint of the first board 1 and the first connection member 11 and the joint of the second board 2 and the second connection member 21, it makes the mechanism of the invention can clamp subjects with any boundary shape.

Figure 10:
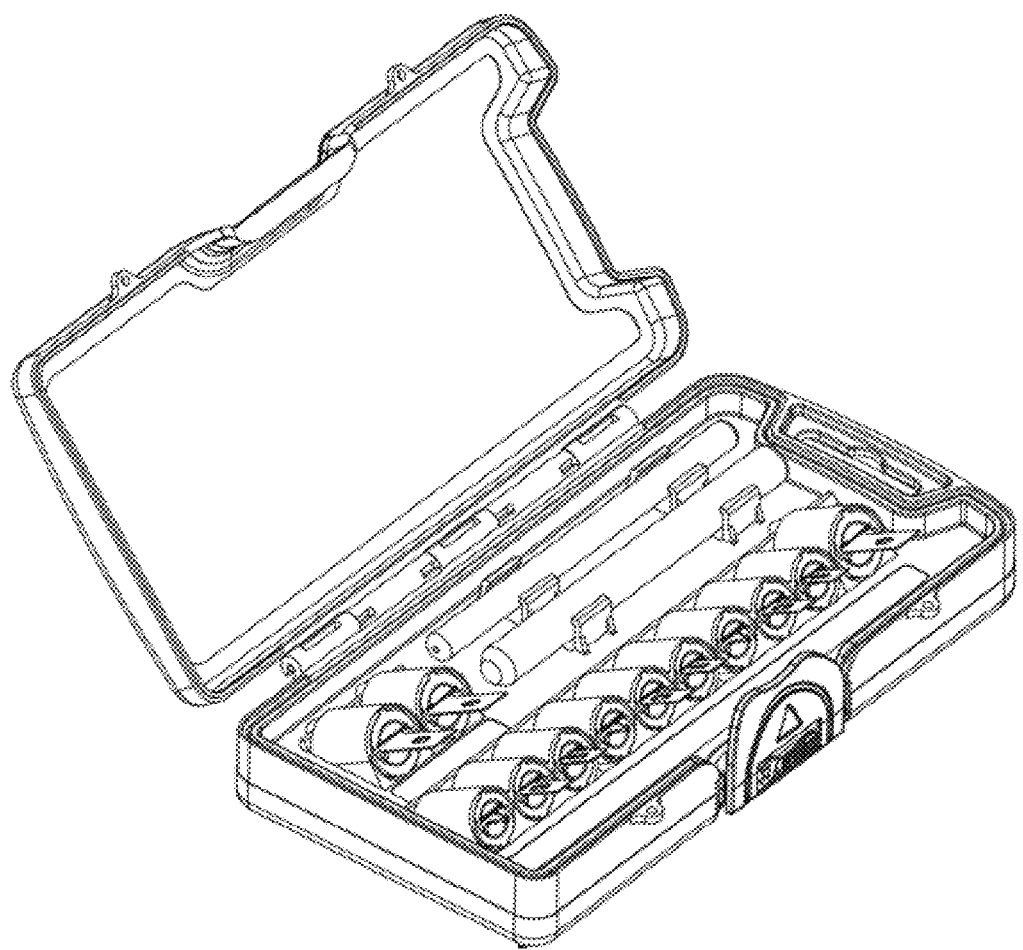
FIG. 10 is a schematic view of a cylinder depositing inside a tool kit of a rotary clamping mechanism of the invention.
Figure 11:
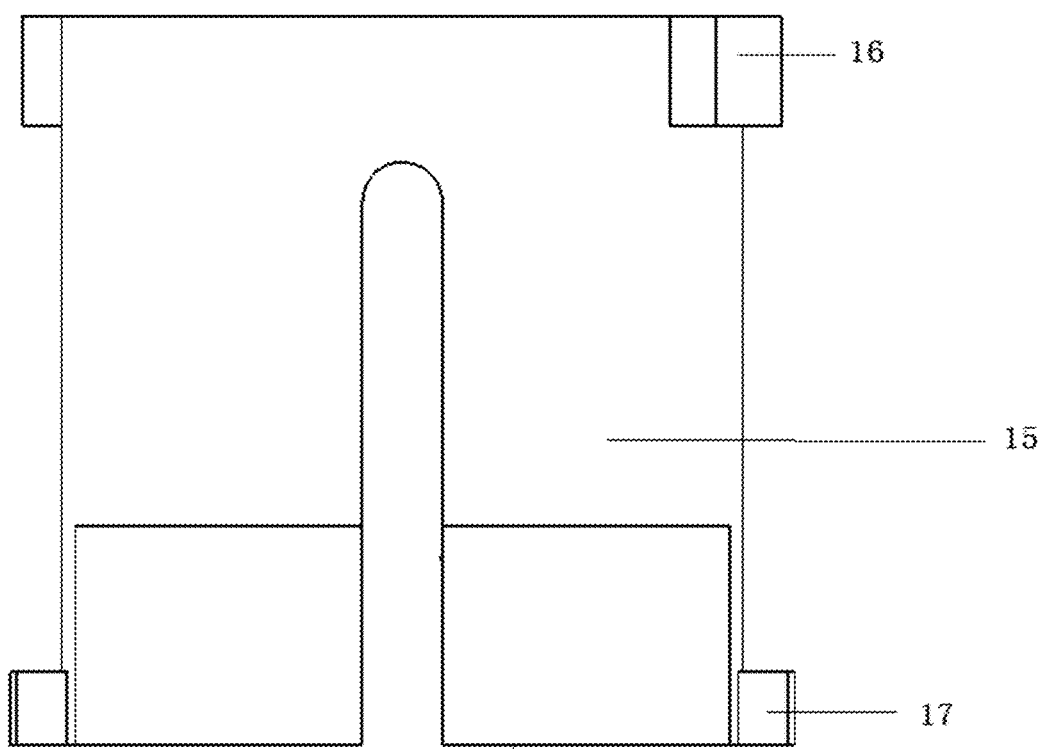
FIG. 11 is a side view of a clamping member of another rotary clamping mechanism of the invention.
Figure 12:
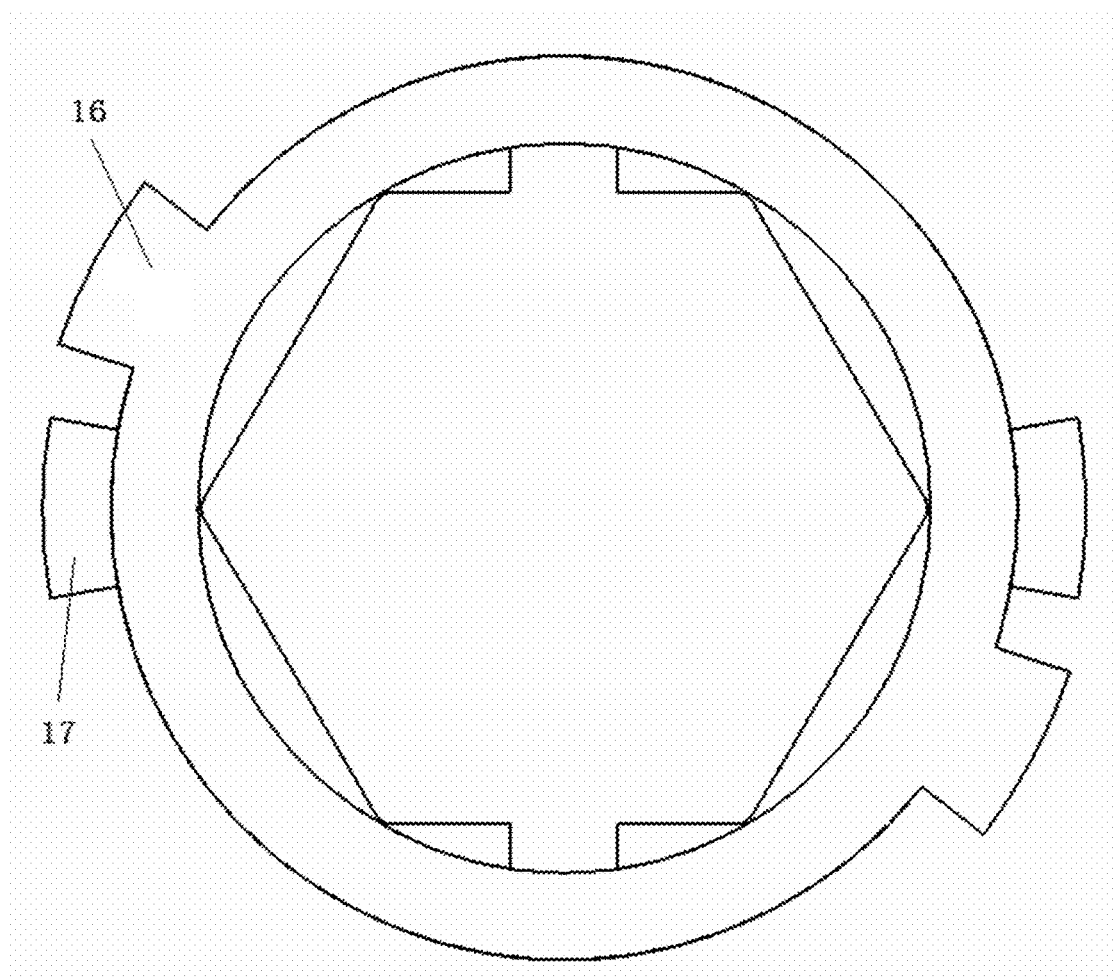
FIG. 12 is a top view of another rotary clamping mechanism of the invention.
Figure 13:
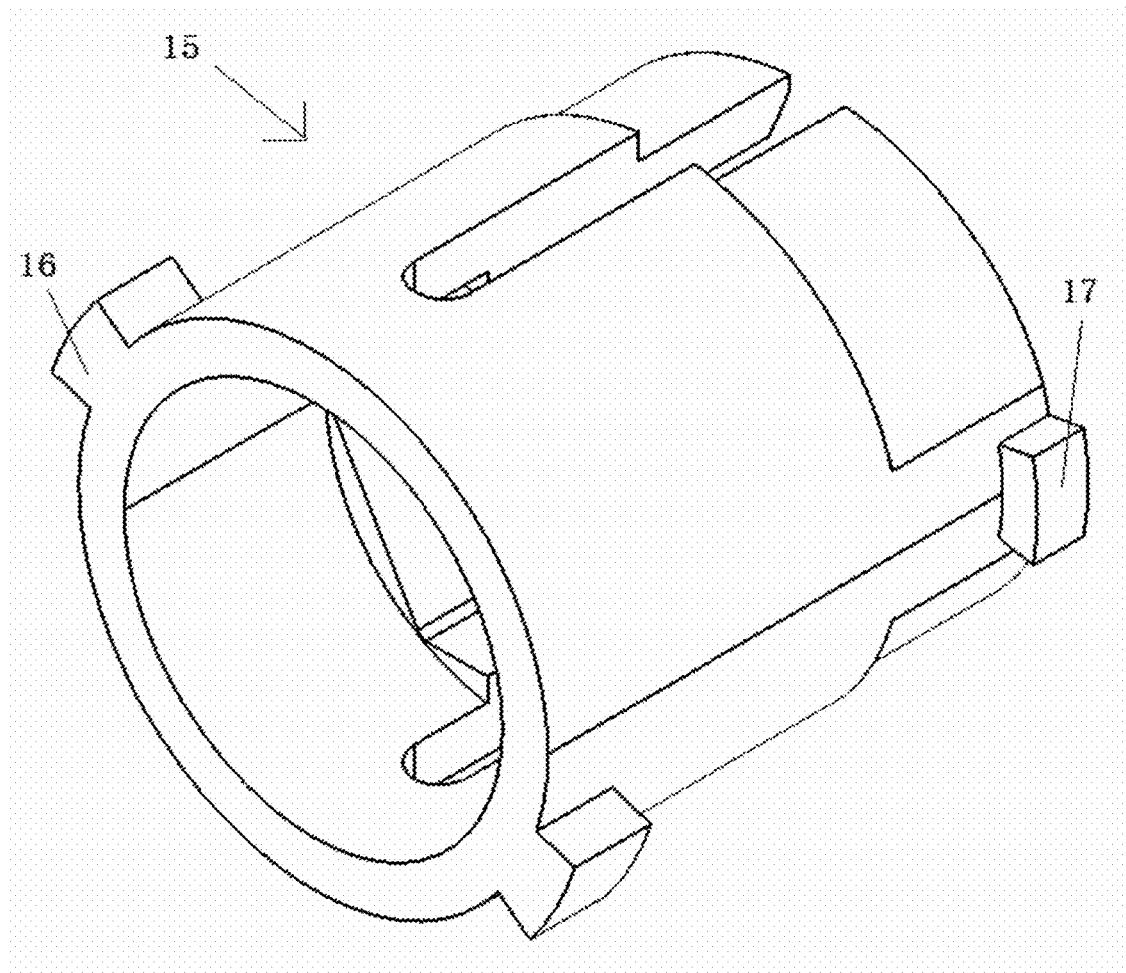
FIG. 13 is a space diagram of another rotary clamping mechanism of the invention.
Figure 14:
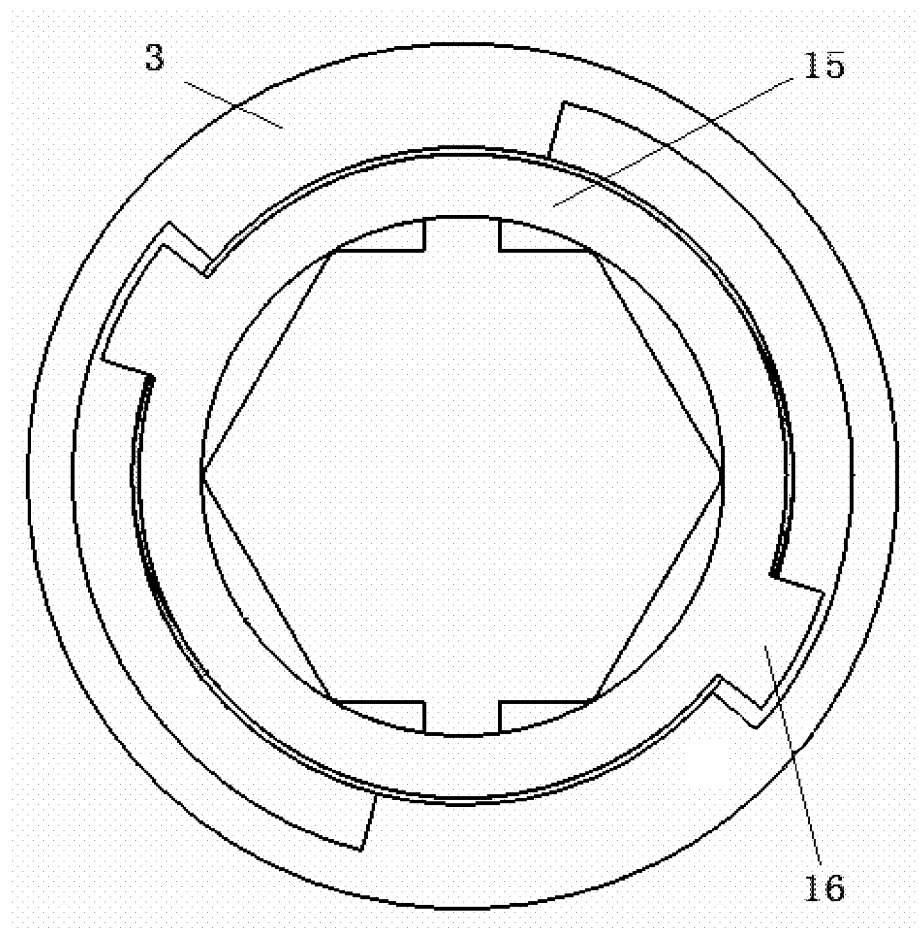
FIG. 14 is a top view assembly drawing of the clamping member and a cylinder of another rotary clamping mechanism of the invention.
Figure 15:
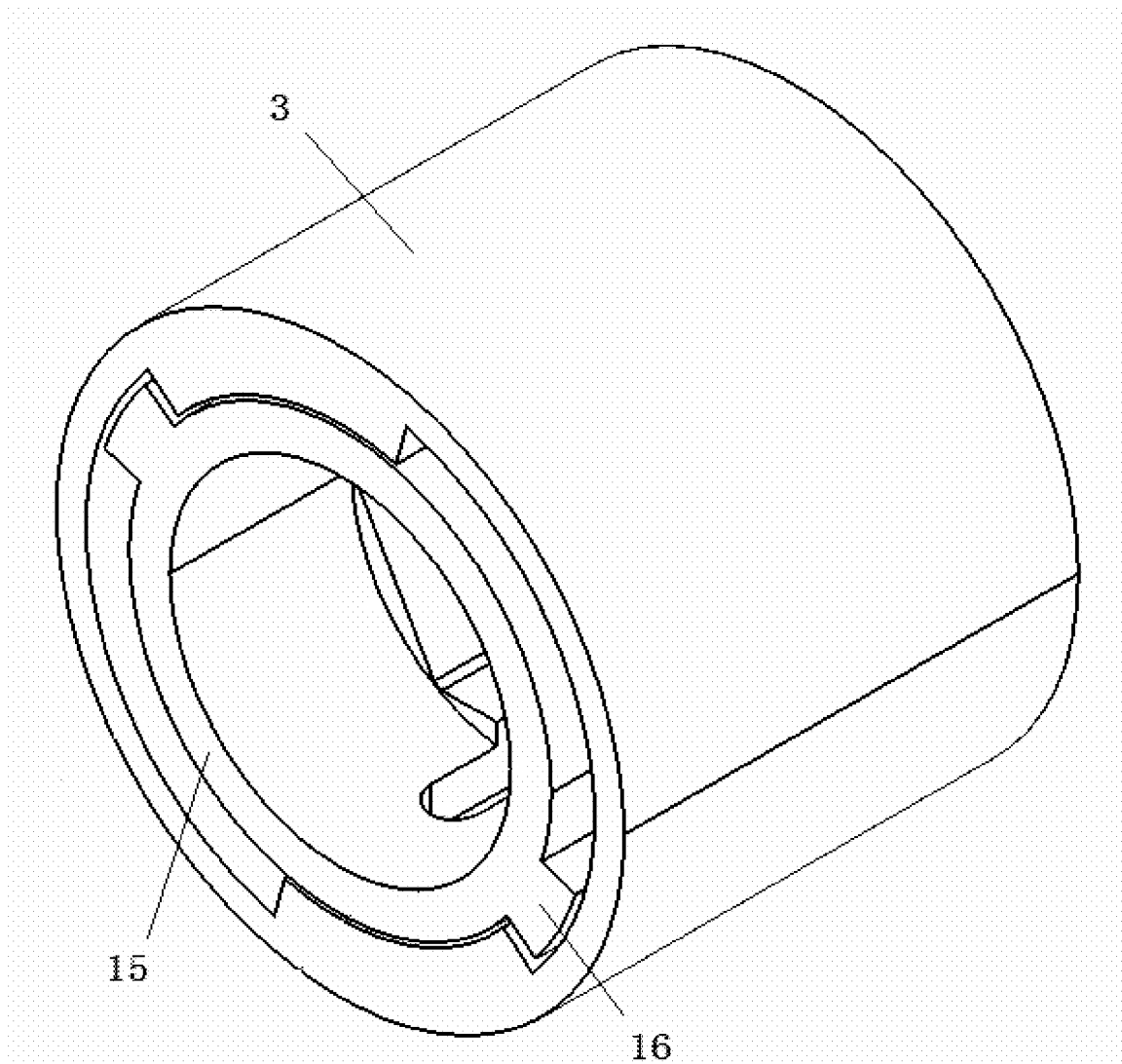
FIG. 15 is an assembly space diagram of the clamping member and the cylinder of another rotary clamping mechanism of the invention.
Figure 16:
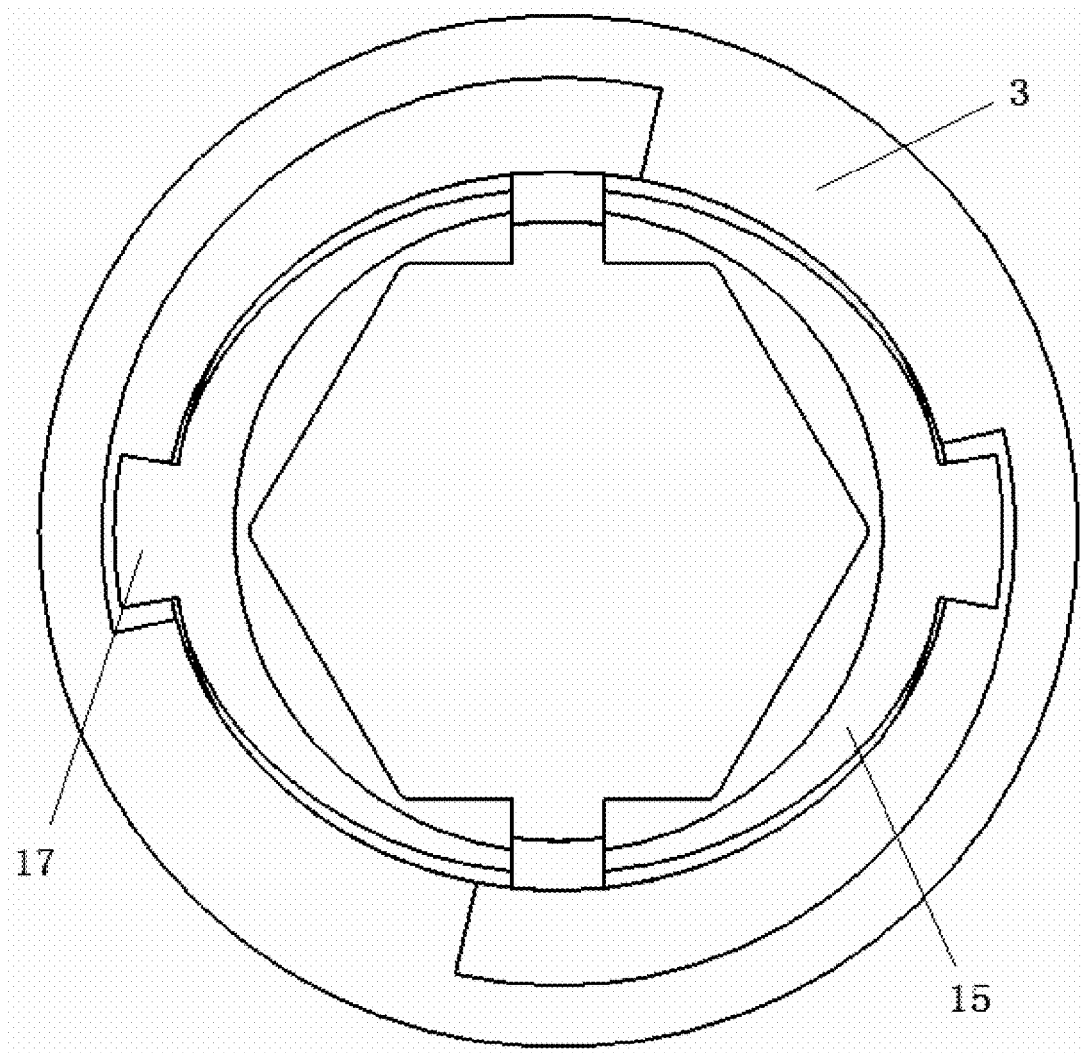
FIG. 16 is an assembly space diagram of the clamping member and the cylinder of another rotary clamping mechanism of the invention.
Figure 17:
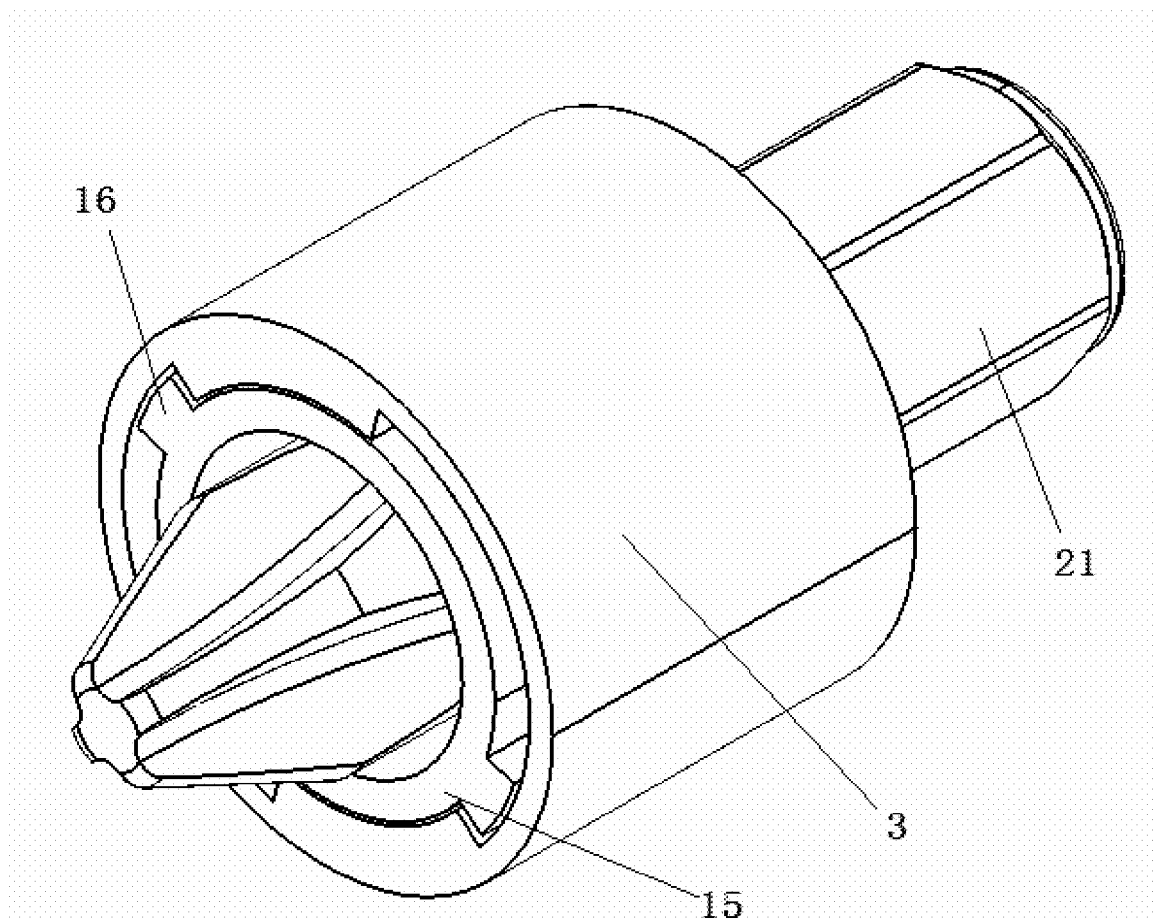
FIG. 17 is a final assembly structure diagram of another rotary clamping mechanism of the invention.

As shown in FIG. 10, in the embodiment, the cylinders 3 are fixed in the tool kit separately to make the process of pulling out a blade able to be done with only one hand, which makes the process much easier.

In another embodiment of the invention, the rotary piece is an integral clamping member 15; an upper part of the clamping member is provided with two upper sliding blocks 16 and a lower part of the clamping member is provided with two lower sliding blocks 17; the two upper sliding blocks 16 and the two lower sliding blocks 17 are symmetry to a center of the rotary clamping mechanism respectively. The upper edge of the inner wall of the cylinder 3 is configured with a wall groove 8; the lower edge of the inner wall of the cylinder 3 is configured with two arc-shaped block 9; two corresponding sides of the upper edge of the wall groove 8 both are configured with arc-shaped grooves 81, and the arc-shaped grooves 81 are configured in a stagger way with the arc-shaped blocks 9.

The specific steps of another embodiment of the invention are shown in FIGS. 11 to 17, wherein configure the clamping member 15 into the cylinder 3; then insert the bit 21 into clamping member 15; then rotate the clamping member 15, and the upper sliding block 16 will slides within the arc-shaped groove 81; once the upper sliding block 16 stops sliding, since the shape of the arc-shaped block 9 of the inner wall of cylinder 3 is oval, the lower block 17 will be limited by the arc-shaped block 9 of the inner wall of the cylinder 3, which makes the clamping member 3 compressed under the force; the bit 21 is fixed by the clamp force generated by the compression of the clamping member 15, and the bigger the compression force to the clamping member 15 is, the bigger the clamp force to the bit 21 is; once the bit 21 is fixed tightly, the tool rod can be pulling out.

FIG. 18 illustrates the basic steps of another embodiment of the invention, to configure the clamp piece 15 in the cylinder 3, and the specific operational steps are shown as follows:

step 1, inserting the a bit into the clamping member;

step 2, rotating the clamping member, and clamping the bit tightly by a convergent force between the lower sliding blocks of the clamping member;

step 3, pulling out the bit from the cutter arbor, and putting the rotary clamping mechanism clamping the blade into a tool kit.

FIGS. 8A to 8B, 9A to 9D all illustrates an integral clamping member, which has the aforementioned technical effects, hence the integral clamping member shown in FIGS. 8A to 8B, 9A to 9D also has the corresponding technical effect, and the specific implementation process thereof are similar to the aforementioned embodiments, hereby not to go into details.

In conclusion, by using the aforementioned schemes, a rotary clamping mechanism and methods for using the same of the invention has the following beneficial effects: blades can be pulled out of cutter arbors easily, and be prevented from rusting caused by touching of hand sweating and blades when depositing blades; meanwhile, it prevents fingers from being scratched; it is easy in operation, and simple in structure which makes the mechanism convenient to manufacture.

While the present disclosure has been described in connection with certain exemplary embodiments, it is to be understood that the invention is not limited to the disclosed embodiments, the device and structure, which are not specifically described, should be understood as the common manner in the art to be implemented; any people skilled in the art can make possible changes and modifications, or equivalents thereof for the technical solution of the invention according to the above methods without falling out of the scope of the invention. Therefore, the various modifications and equivalent arrangements without departing away from the technical solution of the invention, are included within the spirit and the scope of the technical solution of the invention.

What is claimed is:

1. A method for using a rotary clamping mechanism, said rotary clamping mechanism comprises a cylinder and a rotary member, said method comprising placing the rotary member into the cylinder, and further comprising:

step 1: inserting a bit into the rotary member, wherein the rotary member is an integral clamping member, and an upper part of the clamping member is provided with two upper sliding blocks and a lower part of the clamping member is provided with two lower sliding blocks, a wall groove is arranged at a lower side of an inner wall of the cylinder, and a lower side of the rotary member touches against an inside of the wall groove and rotates to contract and compress, and, a lower edge of the inner wall of the cylinder is configured with two arc-shaped blocks, two corresponding sides of an upper edge of the wall groove both are configured with arc-shaped grooves, and the arc-shaped grooves are configured in a staggered manner with the arc-shaped blocks;

step 2: rotating the rotary member, and clamping the bit tightly by a convergent force between the lower sliding blocks of the rotary member, wherein the upper sliding blocks slide within the arc-shaped grooves, and once the upper sliding blocks stop sliding, since a shape of the arc-shaped blocks of the inner wall of the cylinder is oval, the lower sliding blocks are limited by the arc-shaped blocks of the inner wall of the cylinder, which compresses the rotary member and the bit is fixed by a clamp force generated by compression of the rotary member;

step 3: pulling out the bit from a tool arbor, and putting the rotary clamping mechanism clamping the bit into a tool kit.

* * * * *